(12) United States Patent  (10) Patent No.: US 8,778,396 B2
Pillay et al.  (45) Date of Patent: Jul. 15, 2014

(54) MULTI-UNIT GASTRORETENTIVE PHARMACEUTICAL DOSAGE FORM COMPRISING MICROPARTICLES

(75) Inventors: Viness Pillay, Benmore (ZA); Yahya Choonara, Lenasia (ZA); Caragh Murphy, Kennsington (ZA); Sarashnee Moonisami, Sunninghill (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 600 days.

(21) Appl. No.: 12/999,914

(22) PCT Filed: Jun. 3, 2009

(86) PCT No.: PCT/IB2009/005828
§ 371 (c)(1),
(2), (4) Date: Apr. 12, 2011

(87) PCT Pub. No.: WO2009/153632
PCT Pub. Date: Dec. 23, 2009

(65) Prior Publication Data
US 2011/0182988 A1  Jul. 28, 2011

(30) Foreign Application Priority Data
Jun. 19, 2008 (ZA) .................................. 2007/10997

(51) Int. Cl.
| | |
|---|---|
| A61K 9/26 | (2006.01) |
| A61K 9/20 | (2006.01) |
| A61K 9/46 | (2006.01) |
| A61K 9/19 | (2006.01) |
| A61K 31/40 | (2006.01) |
| A61K 31/496 | (2006.01) |
| A61K 31/155 | (2006.01) |
| A61K 9/00 | (2006.01) |
| A61K 31/525 | (2006.01) |
| A61K 31/198 | (2006.01) |
| A61K 31/4178 | (2006.01) |
| A61K 9/24 | (2006.01) |

(52) U.S. Cl.
CPC .................. *A61K 31/198* (2013.01); *A61K 9/19* (2013.01); *A61K 31/40* (2013.01); *A61K 9/2086* (2013.01); *A61K 9/2081* (2013.01); *A61K 31/496* (2013.01); *A61K 9/2077* (2013.01); *A61K 31/155* (2013.01); *A61K 9/0065* (2013.01); *A61K 31/525* (2013.01); *A61K 31/4178* (2013.01); *A61K 9/209* (2013.01)
USPC ........... 424/469; 424/465; 424/474; 424/485; 424/486; 424/487; 424/489; 424/493; 424/497; 424/44

(58) Field of Classification Search
None
See application file for complete search history.

(56) References Cited

U.S. PATENT DOCUMENTS

| | | |
|---|---|---|
| 6,797,283 B1 | 9/2004 | Edgren et al. |
| 2004/0234608 A1 | 11/2004 | Fleshner-Barak et al. |

(Continued)

FOREIGN PATENT DOCUMENTS

| | | |
|---|---|---|
| WO | WO 98/55107 A | 12/1998 |
| WO | WO 2005/079752 A | 9/2005 |

(Continued)

OTHER PUBLICATIONS

Radhakumary, C. et al. Trends Biomat. Artif. Organs (2005), 18(2); pp. 117-124.*

(Continued)

*Primary Examiner* — Kevin S Orwig
(74) *Attorney, Agent, or Firm* — Hamilton, Brook, Smith & Reynolds, P.C.

(57) ABSTRACT

This invention relates to an orally administrable, gastroretentive pharmaceutical dosage form which contains at least one pharmaceutically active ingredient and at least one polymeric adjuvant. The adjuvant serves to retain the dosage form in a selected region of the gastrointestinal tract for sufficient time for the pharmaceutically active ingredient to be released and absorbed. Ideally the dosage form will contain two or more pharmaceutically active ingredients which are delivered to different regions of the gastrointestinal tract.

21 Claims, 4 Drawing Sheets

Schematic of the proposed mechanism of drug release from the gastrofloatable device

(56) References Cited

U.S. PATENT DOCUMENTS

2005/0064027 A1* 3/2005 Jacob et al. .................. 424/451
2005/0249799 A1 11/2005 Jacob et al.
2008/0268045 A1* 10/2008 Dervieux et al. ............. 424/468

FOREIGN PATENT DOCUMENTS

WO   WO 2007/106957 A   9/2007
WO   WO 2008/058288 A   5/2008

OTHER PUBLICATIONS

International Search Report and Written Opinion, PCT/IB2009/005828, mailing date Sep. 22, 2009.

Notification Concerning Transmittal of International Preliminary Report on Patentability, and International Preliminary Report on Patentability, International Application No. PCT/IB2009/005828, mail date Jan. 6, 2011.

* cited by examiner

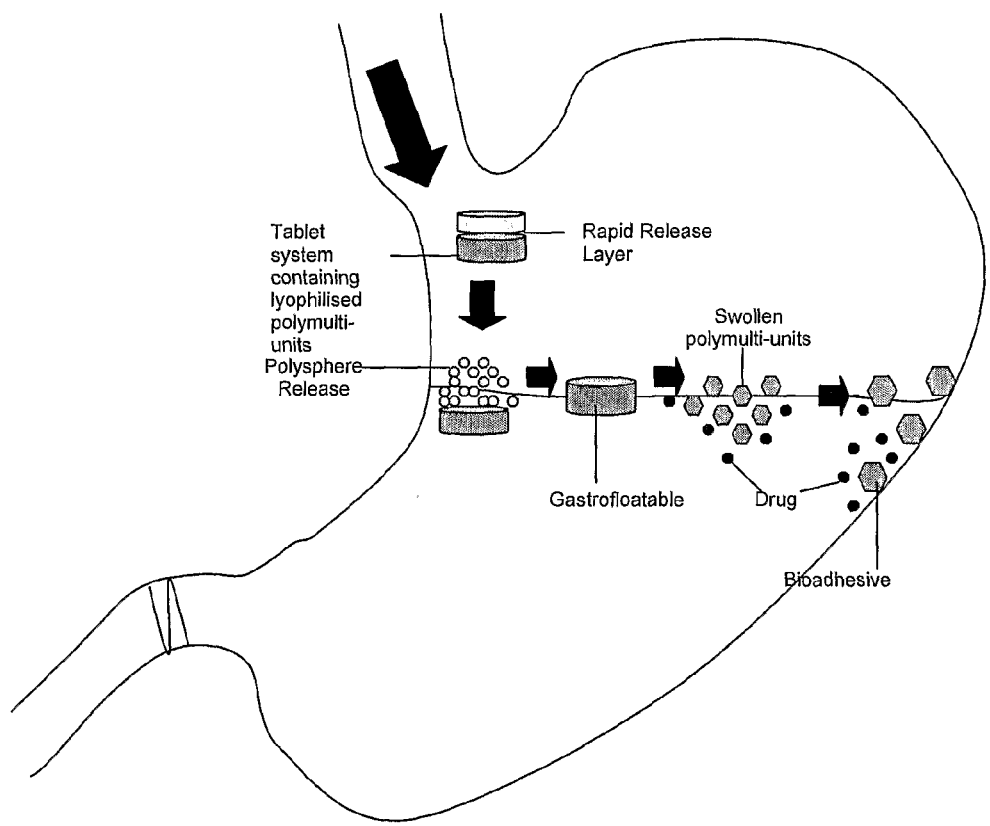
FIGURE 1: Schematic of the proposed mechanism of drug release from the gastrofloatable device

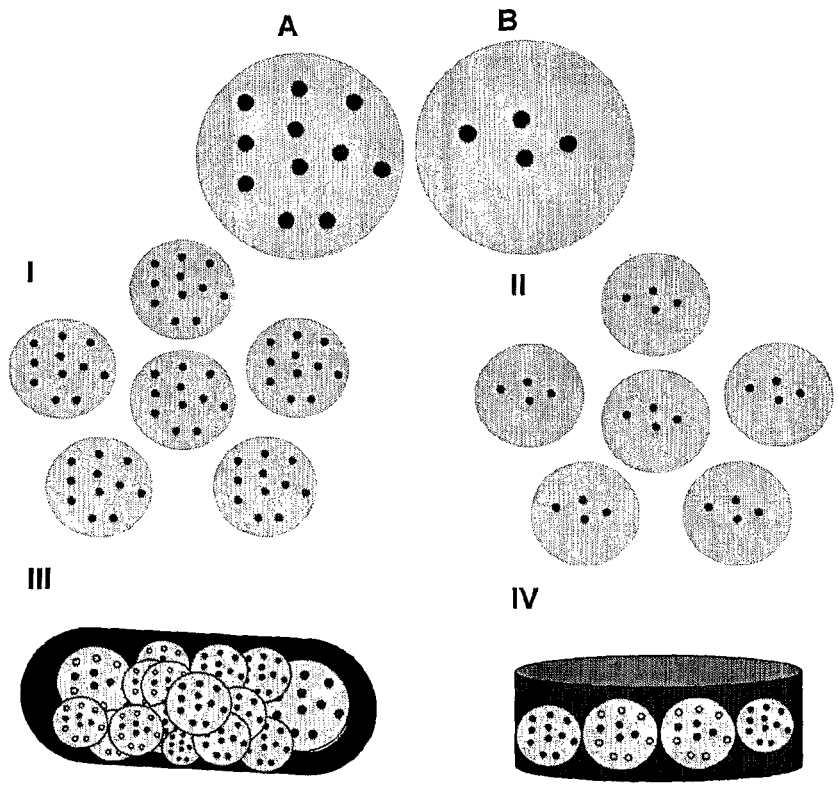
A- Microsphere-loaded multi-units. Pharmaceutical Compositions in either/both components
B- Microsphere and Buoyancy Enhancer-loaded multi-units. Pharmaceutical compositions in either/all components
FIGURE 2: Illustrations of the proposed components of the multi-units that may embed either micro/nanostructures.

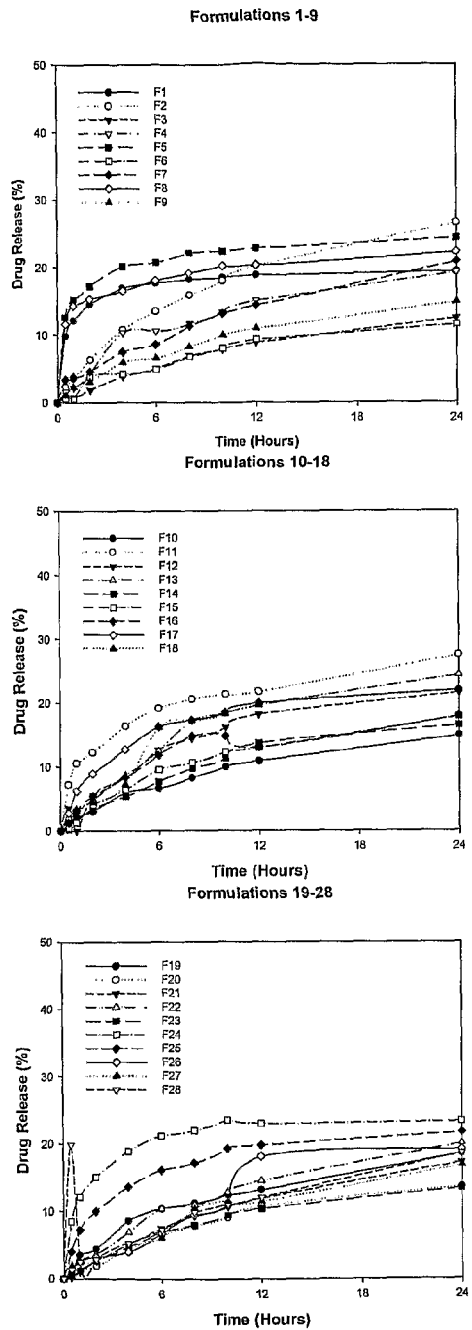
FIGURE 3: Release profiles attained from the gastrofloatable device as per the Box-Behnken design template.

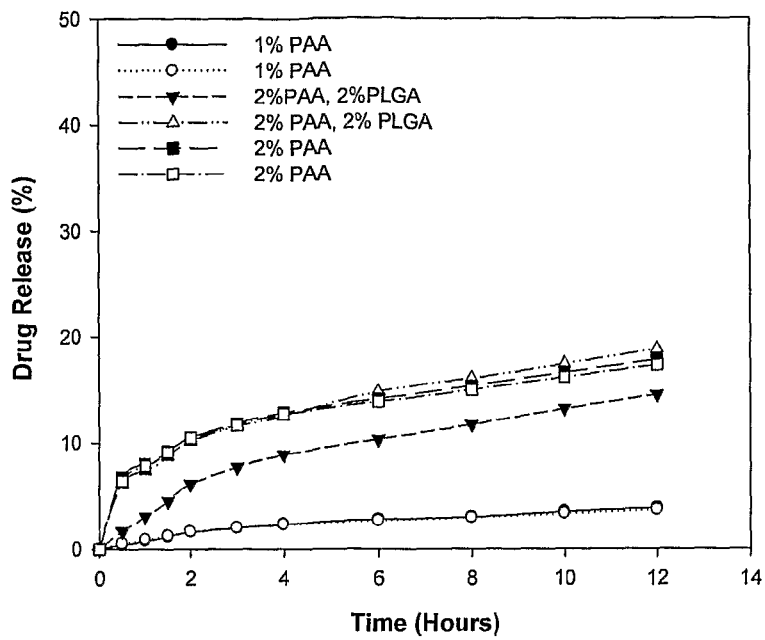
FIGURE 4: Release profiles attained from the gastrofloatable device employing various concentrations of PAA and PLGA and model drug metformin.
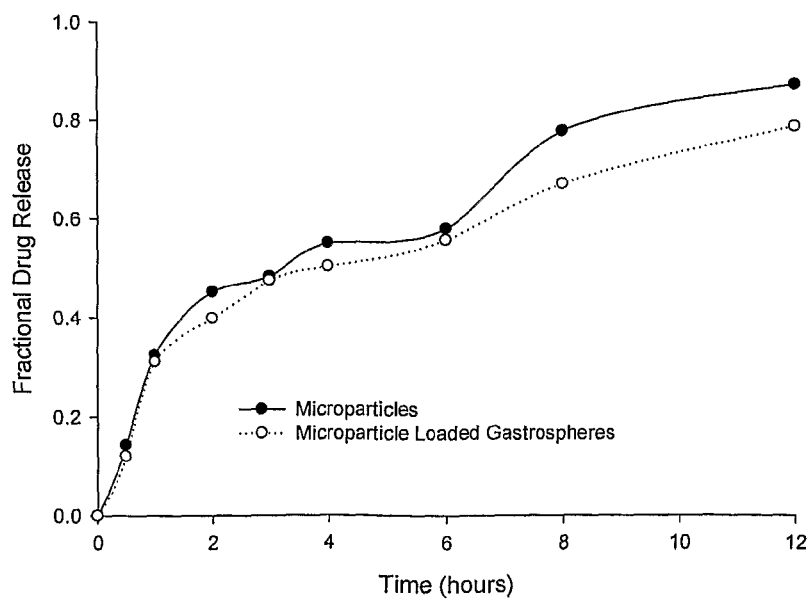
Figure 5: Release profiles attained from the microparticles alone and the microparticles being incorporated within the gastrofloatable device.

US 8,778,396 B2

MULTI-UNIT GASTRORETENTIVE PHARMACEUTICAL DOSAGE FORM COMPRISING MICROPARTICLES

This application is the U.S. National Stage of International Application No. PCT/IB2009/005828, filed Jun. 3, 2009, which designates the U.S., published in English, and claims priority under 35 U.S.C. §§119 or 365(c) to South Africa Application No. 2007/10997, filed Jun. 19, 2008.

FIELD OF THE INVENTION

This invention relates to a pharmaceutical dosage form and, more particularly, to an orally administrable, gastroretentive pharmaceutical dosage form.

BACKGROUND TO THE INVENTION

Oral administration of pharmaceutical compositions still remains a route of choice for most clinical applications. Some drugs have ideal characteristics for good absorption throughout the gastrointestinal tract (GIT) while others present shortcomings in this regard.

In drugs having such shortcomings, the oral route poses a challenge for pharmaceutical compositions that display site-specific absorption. Often such compounds demonstrate poor and variable bioavailability as a result of their small site for absorption within the GIT. These pharmaceutical compositions are said to have a "Narrow Absorption Window" (NAW).

The transit rate of a pharmaceutical dosage form through the GIT determines the time that it remains in contact with its preferred site of absorption. In humans, the transit time in the stomach ranges between one to two hours, in the small intestine remains fairly constant at three hours while, in the colon, this could be as long as twenty hours. Accordingly, for pharmaceutical compositions absorbed in the intestine, the relatively short residence time promotes absorption in the proximal intestine rather than the distal regions. The gastric time determines the duration that pharmaceutical compositions remain in contact with its specific site of adsorption and, therefore, the bioavailability may be enhanced by prolonging the transit time of a pharmaceutical dosage form in the gastrointestinal tract.

Prolonging the release of pharmaceutical compositions within the gastrointestinal tract by way of increasing gastric residence time offers numerous advantages over conventional oral immediate-release drug delivery system as the pharmaceutical composition is released into the stomach and intestines over a longer period of time, allowing more time to be available for pharmaceutical compositions with low bioavailability or narrow absorption windows to be absorbed. Furthermore, free-drug is available for absorption at the "narrow absorption window" region as result of the pharmaceutical dosage form retained for longer in the gastric region with subsequent release of drug before entering the intestine where majority of the "narrow absorption window's" for such drugs are found.

There are numerous factors which affect gastric emptying and, as a result, may influence the gastric retention time of a pharmaceutical dosage form. The size and shape of such a pharmaceutical dosage form affects the transit through the pyloric sphincter, while its density determines its gastrofloatibility (resulting in buoyancy on gastric contents) or gastroimmensity (resulting in sinking toward the antrum of the gastric region). These factors are important to consider when designing a GIT drug delivery system.

Biological factors also play an important role in the functioning of the GIT and, consequently, the uptake kinetics of an orally administered pharmaceutical compaction. These biological factors include the age and gender of the patient, the presence of disease as well as their level of physical activity, body mass index and posture. Further factors that influence gastric emptying include the ingestion of food and particular drugs which may have an impact on GIT motility.

OBJECT OF THE INVENTION

It is an object of this invention to provide an orally administrable gastroretentive pharmaceutical dosage form, more particularly, a gastroretentive pharmaceutical dosage form that, at least partly, addresses the above-described shortcomings

SUMMARY OF THE INVENTION

In accordance with this invention, there is provided an orally administrable, gastroretentive pharmaceutical dosage form comprising at least one pharmaceutically active ingredient and at least one polymeric adjuvant which enhances retention of the or each pharmaceutically active ingredient in a predetermined region of the gastrointestinal tract.

There is also provided for the pharmaceutical dosage form to be a multi unit dosage form which incorporates micro and/or nanostructures, for the pharmaceutical dosage form to be in the form of a tablet which, on hydration, becomes buoyant.

There is further provided for the pharmaceutically active ingredient to be released continuously at a slow rate prior to reaching its absorption window thereby ensuring optimal bioavailability in use.

There is also provided for the polymeric adjuvant to be a gastrofloatable and/or bioadhesible enhancing composition, for the composition to prolong, in use, the residence time of the dosage form in the gastrointestinal tract, and consequently of the or each pharmaceutically active ingredient.

There is further provided for the pharmaceutically active composition to have a poor bioavailability or narrow absorption window and for the pharmaceutically active compound to be selected from the group consisting of acyclovir with an absolute or relative bioavailability of 23%, captopril, preferably with an absolute or relative bioavailability of 65%, riboflavin, preferably with an absolute or relative bioavailability of 15%, levodopa, preferably with an absolute or relative bioavailability of 30%, nitrofurantoin, preferably with a bioavailability of 40% and ciprofloxacin, preferably with an absolute or relative bioavailability of 69%.

There is also provided for the pharmaceutically active ingredient or ingredients to be mixed with the polymeric adjuvant or adjuvants as a homogenous blend, alternatively for the pharmaceutically active ingredient or ingredients and polymeric adjuvant or adjuvants to have a multi-unit structure with at least one operatively inner component and an operatively outer component with the operatively inner and outer components consisting of either a pharmaceutically active ingredient, alternatively a polymeric adjuvant, further alternatively a blend of a pharmaceutically active ingredient and polymeric adjuvant.

There is further provided for the pharmaceutical dosage form to be both gastrofloatable and bioadhesive, in use, for the pharmaceutical dosage form to be initially buoyant on the surface of gastric contents and, as the gastric contents pass through the stomach and move into the intestine, for the dosage form to adhere to the mucosal surface of the stomach thus extending the length of time for which the pharmaceutical dosage form is retained within the stomach and, consequently, increasing the retention time of the pharmaceutically active ingredient or ingredients in the stomach.

There is also provided for the dosage form to incorporate microstructures or nanostructures which include a bioadhesive polymeric adjuvant as well as at least one pharmaceutically active ingredient and which are released as the gastric contents move into the intestine and adhere to the mucosal surface of the stomach thus extending the length of time for which the pharmaceutical dosage form is retained within the stomach and, consequently, increasing the retention time of the pharmaceutically active ingredient or ingredients in the stomach.

There is also provided for a polymer to be crosslinked in a desirable electrolyte or salt solution with electrolytes or salts being selected from but not limited to a salt from the Hofmeister Series of salts to produce the multi-units.

There is also provided for the pharmaceutical dosage form to be in the form of an orally ingestible tablet which effervesces, in use, when in contact with gastric contents thus allowing the dosage form to become less dense and migrate to the surface of the gastric contents.

There is also provided for the pharmaceutical dosage form to be in the form of an orally ingestible tablet containing a multiplicity of polymeric multi-units and which, when contact is made with gastric contents, releases the polymeric multi-units which hydrate and swell to reduce the density of the multi-units and, consequently, enable the multi-units to remain buoyant on the surface of the gastric contents and, later, to adhere to the mucosal lining of the stomach, either before or after the gastric contents move into the intestines.

There is also provided for the pharmaceutical dosage form, alternatively the multi-units, to be coated with a rate-modulated release coating which, in use, allows the pharmaceutically active compound or compounds to be released over an extended period of time.

There is also provided for the inner multi-unit component to be mixed with a pharmaceutically active compound or compounds, excipients and/or permeation enhancers.

There is also provided for the pharmaceutical dosage form to be in the form of a tablet and for the tablet to have a plurality of layers, each layer having an inert, alternatively at least one pharmaceutically active compound and at least one biodegradable polymer which biodegrades in use to release the pharmaceutically active compound or compounds at a predetermined release rate depending on the biodegradability of the polymer.

There is further provided for the polymeric adjuvant to be a standard hydrophilic polymer, alternatively a hydrophilic swellable or erodible or bioadhesive polymer, further alternatively a standard hydrophobic polymer, still further alternatively a hydrophobic swellable/erodible/bioadhesive polymer, and, preferably, one or more polymers selected from the group comprising of: hydroxyethylcellulose (HEC), hydroxypropylcellulose (HPC), hydroxypropylmethylcellulose (HPMC), polyethylene oxide (PEO), polyvinyl alcohol (PVA), sodium alginate, pectin, ethylcellulose (EC), poly (lactic) co-glycolic acids (PLGA), polylactic acids (PLA), polymethacrylates, polycaprolactones, polyesters, polyacrylic acids and polyamides.

There is also provided for the polymers to be mixed with a co-polymer or used alone in the pharmaceutical dosage form.

There is also provided for the polymers to be selected to achieve, in use, a zero-order, a first-order and a burst release of one or more pharmaceutically active ingredients over a twelve hour period.

There is also provided for the said pharmaceutical dosage form to be applied for the local treatment of conditions related to the gastrointestinal tract.

The invention extends to a method of producing an orally administrable, gastroretentive pharmaceutical dosage form in the form of an orally administrable tablet, each tablet comprising a multiplicity of multi-units each having at least one pharmaceutically active ingredient and at least one polymeric adjuvant which enhances retention of the multi-unit and, consequently of the or each pharmaceutically active ingredient in a predetermined region of the gastrointestinal tract, the method including lyophilizing the multi-units before or after incorporation into the tablet.

There is also provided for the lyophilized multi-units to have a porous structure which, in use, reduces the density of the multi-units and allows allowing them to remain buoyant in the gastric region.

There is also provided for the density of the gastroretentive pharmaceutical dosage form to be less than 1 $g/cm^3$, in use, thus allowing the dosage form to become buoyant upon contact with the gastric contents, for the density of the dosage form to be a function of the porosity of the dosage form and for the porosity of the dosage form to be adjusted during its production by adding pore forming excipients and/or adjusting the lyophilization process.

There is further provided for the mucoadhesive nature of the gastroretentive pharmaceutical dosage form to be as a result of the incorporation of suitable polymers, preferably polyacrylic acid and/or as a result of electrostatic interactions, hydrogen bonding, hydrophobic interactions, and inter-diffusion between the gastroretentive pharmaceutical dosage form and the gastrointestinal tract.

There is also provided for the mucoadhesive nature of the gastroretentive pharmaceutical dosage form, preferably in the stomach, to be a function of an extended macromolecular network, significant hydration, the number of carboxyl groups, as well as the presence of ionic charges.

There is further provided for the gastroretentive pharmaceutical dosage form to have a rigid matrix constituted by polymers and excipients, preferably polymers and excipients selected from the group consisting of zinc, calcium, alginate, pectin and PLGA, for the polymers and excipients form to have a pKa between 3 and 4, and for the polymers and excipients to operate by decreased dissociation of H+ ions which results in greater hydrogen bonds in process on contact with the gastric contents.

There is also provided for the polymers and excipients constituting the rigid matrix of the gastroretentive pharmaceutical dosage form to form, in use, an outer barrier of variable thickness and erosion kinetics which, in use, influence the rate of drug release from the said gastroretentive pharmaceutical dosage form.

BRIEF DESCRIPTION OF THE FIGURES AND TABLES

Embodiments of the invention will be described below by way of example only and with reference to the accompanying Figures in which:

FIG. 1: is a schematic of the proposed mechanism of drug release from the gastrofloatable device;

FIG. 2: are illustrations of proposed components of multi-units that may embed micro structures of nanostructures;

FIG. 3: shows release profiles attained from a gastrofloatable device as per the Box-Behnken design template;

FIG. 4: shows release profiles attained from a gastrofloatable device employing various concentrations of PAA and PLGA and the model drug, metformin, and FIG. 5: shows release profiles attained from a) microparticles alone and b) microparticles incorporated within the gastrofloatable device.

DESCRIPTION OF THE PREFERRED EMBODIMENTS

Floatation of drug delivery systems as a gastroretentive mechanism has been widely used. These systems, also known as hydro-dynamically balanced, are buoyant on the gastric fluid and delay their emptying through the pyloric sphincter by swelling and expanding. Buoyancy is a result of a reduction in matrix density (Kwon and Singh, 1998; Yasunori et al., 2004). Floatable delivery systems have been designed as single and multiple-unit devices (Whitehead et al., 1999), the latter seldom used due to formulation challenges. Single unit systems have serious limitations such as inadequate gastroretention, variable swelling and motility in the fasted and fed states, and poor mechanical integrity. On the other hand, multiple-unit floatable systems are advantageous due to the following attributes:
(i) their ability to overcome the "all or nothing" gastric emptying behaviour of single-unit systems;
(ii) they provide a more predictable release profile;
(iii) they do not significantly impair the performance of the device since failure of one unit does not comprise the efficacy of the entire system; and
(iv) their ability to accommodate more than one drug, with each having different release rates.

To date, no research has reported on the pharmaceutical performances of a crosslinked, multiple-unit, consolidated gastroretentive device. The overall aim of this study was to develop a multiple-unit gastrofloatable device that would provide a prolonged release rate for the model drugs riboflavin and metformin.

All polymers considered for the system are biodegradable and biocompatible and have bioadhesive and swelling properties. Bioadhesive polymers interact with the mucosal lining of the stomach in varying ways. These include ionic, hydrogen, disulfide and physical bonds. Polymers investigated included those in the cellulose class, namely hydroxypropylmethylcellulose as well as alginate, chitosan, pectin, poly (lactides) and glycolides, PLGA, poly(methacrylate) and poly(acrylic acid) polymers. Polymers, crosslinking agents and excipients were all of analytical grade.

A gastrofloatable and bioadhesive prolonged-release drug delivery system can be developed either as a single or multiple-unit formulation. The major disadvantage of a single-unit formulation is their 'all-or-nothing' emptying process, which could lead to a high variability in bioavailability and gastric irritation. However, multi-unit drug delivery systems offer more reproducible gastric residence times, reduced absorption variability between subjects and offer a superior dispersion pattern through the gastrointestinal tract, resulting in a reduced risk of damage to the local mucosa. Mucoadhesive drug delivery systems have not yet reached their full potential to deliver drugs within the gastro-intestinal tract due to the failure to achieve sufficient prolonged controlled release of drugs.

Polymers suitable for gastroretentive pharmaceutical dosage forms were identified based on publicly available information provided in literature. The aim of this study was to develop a multiple-unit gastroretentive pharmaceutical dosage form employing a lyophilized, swellable polymeric multi-unit system incorporated within an outer tablet-like device. Riboflavin, and metformin, was the model narrow absorption window pharmaceutically active compounds used to assess the prolonged rate of release from the gastroretentive device (FIG. 1).

A Box-Behnken statistical design template of 27 random experimental runs and three centre points was built using Minitab (USA). Polymeric matrices were formulated with variable concentrations and combinations of polymers, preferably sodium alginate, pectin, polylactic co-glycolic acid and polyacrylic acid. Pharmaceutically active compound/s were added in various ratios, preferably a 2:1 ratio (polymer: drug) to the polymeric dispersion. Gelification was employed to formulate crosslinked polymeric, bioactive-loaded multi-units, preferably multi-units in accordance with the statistical design.

To optimize the buoyancy of the multi-units, each formulation was exposed to pre-determined periods of lyophilization. The drug incorporation efficiency of the pharmaceutically active compound/s was determined spectrophotometrically. In vitro assessment of the drug release, determination of the rigidity of matrices and observation of the buoyancy of the system was performed in simulated gastric fluid of pH 1.2 and phosphate buffer pH 6.8.

Preparation of the multi-units involved a homogenized polymeric solution comprising varying concentrations of Protanal (alginate), pectin, PAA, PLGA and metformin that was crosslinked in a solution of zinc gluconate or calcium hydroxide. The multi-units were left overnight (zinc gluconate) or for 20 minutes (calcium hydroxide) to cure and washed thrice with deionized water. They were then frozen for 24 hours at −72° C. and lyophilized at −60° C. at 25 mtorr for 24 hours.

Microparticles preparation involved the emulsification of an aqueous chitosan solution into an organic poly(methacrylate) solution. The resultant emulsion was ionically crosslinked using a crosslinker. Microparticles were washed, filtered and air dried and incorporated within the gastrospheres.

Two other formulation approaches were also investigated; the first involved a water/oil/water double emulsion, while the second involved ionic gelification. A double W/O/W emulsion method was employed, making use of various classes of polymers. Solutions of the above mentioned polymers were prepared with the use of an organic solvent such as dichloromethane. An aqueous solution of drug was then added to the first polymeric solution in order to develop a primary W/O emulsion. The primary emulsion was then slowly injected into the second polymeric solution under agitation, producing a final W/O/W double emulsion. Excess organic solvent was evaporated and the remaining emulsion filtered and lyophilized.

For the ionic gelification approach, model drug riboflavin was added to a polymeric solution comprising either sodium alginate, pectin and/or polylactide co-glycolide in a 2:1 ratio (polymers:drug). Chitosan, mannuronates and guluronates were dissolved in 100 mL de-ionized water. The dispersion was covered to prevent any exposure to light and stirred for 1 hour. Thereafter, a granular mixture of poly(lactide co-glycolide) was added to the dispersion as a consolidator. The poly(lactide co-glycolide) is insoluble in de-ionized water and, therefore, homogenized to form a uniform multi-polymeric dispersion. A solution for the gelification of the drug-polymer dispersion comprised either calcium chloride, magnesium sulphate or a combination selected from the Hofmeister Series. Using a peristaltic pump, the drug-polymer solution was slowly titrated at a rate of 1 mL/min in the gently stirring gelification solution. On completion of the process, the crosslinked multi-units were allowed to stir in this solution for an additional 45 minutes filtered, washed and lyophilized. After this period, they were filtered and washed with de-ionized water. In their hydrated state, the multi-units were introduced into plastic trays and subjected to lyophilization.

Lyophilization assisted with the buoyancy of the multi-units by increasing their porosity, thereby reducing the overall density of the drug delivery system. The formed multi-units were lyophilized under the following conditions: −60° C. for 2 hours, followed by a vacuum of 40 mtorr for 24 hours.

A suitable polymer, soluble at a pH of ±1.2, was used. Two stages of coating were employed, making use of a DIOSNA MiniLab® Fluid Bed Processor (DIOSNA, Osnabruck, Lower Saxony, Germany). First, the multi-units were coated with varying thicknesses of the polymer in order to stagger the release of the drug. The second stage involved the coating of the entire tablet drug delivery system, ensuring that effervescence, swelling and adhesion did not occur before the tablet entered the stomach.

A double layer tablet was prepared using a MiniPress Tablet Press (DIOSNA, Osnabruck, Lower Saxony, Germany). The first layer comprised the effervescent disc while the second layer contained the drug loaded multi-units. Other excipients, such as lactose and sterilized talc, were included as lubricants and diluents (FIG. 1).

A Box-Behnken Design, composed of four factors, 27 random experimental runs and three centre points, was built using Essential Regression of Experimental Design V2.207 (Pennsylvania, USA) software. The formulation variables tested included the concentration of polymers, while the lyophilization time constituted an important process variable. Ideally the polymers were tested from 0.25-2% w/v. The lyophilization time ranged from 2-24 hours.

In order to visualize the surface structures and the occurrence of pores within the structure, the morphology and dimensions of the formed multi-units were analyzed by the Scanning Electron Microscope (SEM) (JEOL, Tokyo, Japan).

In order to determine the amount of drug entrapped within the multi-units, the efficacy of drug loading was measured. Drug entrapment studies were, therefore, conducted. A sample of the multi-units was dissolved in simulated gastric fluid and left for 24 hours to ensure complete extraction. The solution was filtered and the amount of drug present was determined using Ultra Performance Liquid Chromatography (UPLC). Each determination was performed in triplicate.

Multi-units were stored in vacuum chambers at different temperatures and humidity conditions in the absence and presence of fluorescent light. Typical conditions used included 5° C., 21° C., and 37° C. with 75% relative humidity. The study was conducted over a period of three months. A UPLC method was developed to analyze both intact drug and degradation products of the model drugs employed. In addition to UPLC, moisture content of the multi-units was analyzed using a Karl-Fischer apparatus. Buoyancy of the multi-units was observed visually. The time lapsed for the multi-units to become buoyant (lag time) and the duration of buoyancy was noted.

Approximately 50 mg of multi-units was dissolved in monobasic phosphate buffer pH 6.8. Dissolution of the multi-units was facilitated by triturating them before addition to the buffer. The solution was filtered and the concentration of drug was spectrophotometrically measured. Each determination was performed in triplicate. Release studies were conducted in a fully calibrated six-station dissolution test apparatus, using the USP 23 Apparatus in the USP-recommended buffers (pH 1.5, 4, 6.8; 900 mL; 37±0.5° C.). All studies were conducted in triplicate using an automated sampling procedure. Drug release was determined using a UPLC.

In yet another dissolution study, a sample of multi-units weighing 200 mg was capsulated. Drug release was determined employing the USP 1 method over a duration of 12 hours in simulated gastric fluid pH 1.2 maintained at 37° C. 5 mL samples were taken at predetermined time intervals and the dissolution medium was replaced with drug-free buffer in order to maintain sink conditions. Samples were analyzed by UV spectroscopy (FIG. 1).

To determine the effect of a continuous pH change with time (i.e. simulated gastrointestinal pH variation), dissolution studies were performed at 37±0.5° C. using the USP 25 Apparatus 3 (Bio-Diss II Release Rate Tester, Vankel Industries) and buffers of different pH (220 mL per vessel). Simulated gastric fluid was prepared, containing sodium chloride, pepsin, hydrochloric acid and deionised water. The formulation was subjected in duplicate to a continuous run for 12 hours each at pH 1.5 and 4 and 6.8. The standard oscillation rate of 10 dips per minute (dpm) was employed throughout the study. Time intervals at which samples were taken and concentrations were determined at 0, 0.5, 2, 4, 6, 10, 12, 18 and 24 hours.

For the determination of swelling, samples of the multi-units were placed in a glass vial containing 10 mL of simulated gastric fluid and maintained at 37° C.±0.5° C. Swollen multi-units were periodically removed and weighed. The experiment was conducted in triplicate. The percentage of polymer swelling was calculated from Equation 1:

$$\frac{\text{Final mass of beads } (W_t) - \text{initial mass of beads } (W_o)}{\text{Initial mass of beads } (W_o)} \times 100 \qquad (1)$$

The buoyancy characteristics of the drug delivery system were determined by visual inspection with the use of a rotating paddle apparatus in simulated gastric fluid maintained at 37±0.5° C. The time interval between the introduction of the multi-units into the dissolution medium and their buoyancy to the top of the medium was taken as the buoyancy. The duration of buoyancy was also recorded. The buoyancy lag time and the duration of buoyancy was determined in hydrochloric acid buffer pH 1.5, and for comparative purposes, in phosphate buffer pH 6.8 lag-time and the duration of system floatation was visually observed.

Textural analysis was conducted using a Texture Analyzer (Stable Microsystems, Surrey, UK), equipped with Texture Exponent V3.2 software package. Bioadhesion and resilience of the drug delivery system were determined.

In order to evaluate the bioadhesion of the drug delivery system, the tensile force required to separate the polymer from a portion of freshly excised rabbit stomach was determined. Portions of stomach tissue were secured to the probe and the probe was lowered until it made contact with the tissue mount, and the force required to remove the polymer was determined from the Force-Time curve. The experiment was conducted in triplicate.

As compression may be an option involved in the tableting the multi-units, the multi-units should be sufficiently resilient. The multi-units were, therefore, subjected to resilience measurements. Porosity was quantitatively analyzed by the textural profiling of the multi-units.

Multi-units were hydrated in hydrochloric acid buffer pH 1.5 and phosphate buffer pH 6.8 over a period of 24 hours. At pre-determined times; samples were removed and subjected to a load of 40N controlled by a 5 kg loadcell. The Force-Displacement profiles were generated and analyzed for the degree of matrix deformation. These studies were achieved using a Texture Analyzer. The lag phase of the Force-Displacement profile provided an indication of peripheral gel growth and could therefore be converted to the degree of swelling. The swelling ratio (SR) was also calculated using Equation 2:

$$SR=(W_e-W_0)/W_0 \qquad (2)$$

Where $W_o$ is the initial mass of the dry multi-units and $W_e$ is the mass of the swollen multi-units at equilibrium swelling in the media. Each experiment was repeated thrice and the average value+/- standard deviation was taken as the SR value.

The rheology of the hydrated system was assessed using a Thermo-Haake MARS Rheometer. Samples were placed into simulated gastric fluids within a water bath in order to achieve a biological temperature of 37±0.5° C. As soon as the desired temperature was reached, samples were removed from the water bath and mounted onto the rheometer stage for flow-curve analysis. The viscosity was measured after the sensor had rotated a minimum of 5 rpm. All measurements were conducted in triplicate. Recording the dimensional stability of the drug delivery system was important for reproducibility. Dimensional stability is a measurement of the linear dimensional change resulting from exposure to temperature. Dimensional stability was observed visually in simulated gastric fluid using the dissolution apparatus.

Analysis of Variance was conducted on each of the responses (i.e. dependent variables) at a 95% confidence interval in order to determine the level of interaction among the independent variables (main effects). Since a quadratic design was used, the following indices were monitored: $R^2$, Durbin-Watson Statistic and PRESS Index to ensure model suitability and stability. In addition, drug release kinetics was analyzed as per Power Law, Hopfenberg Model and Peppas-Sahlin Relaxational Equation.

Box-Behnken designs are often used to study response surfaces. The design is usually formed to allow a quadratic response surface to be fitted. The factors are studied at three equally-spaced levels, denoted by −1, 0 and 1. The construction uses a balanced incomplete block design to select successive sets of factors to be applied at all factorial combinations of −1 and +1, while other factors are held at 0. The p-values at a 95% confidence interval (ANOVA) generated by Essential Regression and Experimental Design V2.207 provided information on the significance of the interactions between the independent and dependent variables. Preliminary tests were conducted to determine the reproducibility of the formulation process using a maximum coefficient of variation (CV) of 0.1 as acceptance criteria. Statistical parameters that were used to assess the goodness-of-fit of the Box-Behnken Design for each response (dependent variable) included the correlation coefficient ($R^2$), Precision Index and Anderson-Darling Statistic. Multi-unit formulations with and without polyacrylic acid (PAA) were immediately buoyant and remained buoyant for greater than 72 hours. Bioadhesivity results indicated that the addition of PAA into the alginate-pectin multi-unit formulation resulted in a more favorable bioadhesion profile. Formulations containing PAA displayed a gradual increase in bioadhesion, showing an initial peak after 4 hours, thus revealing that adhesion increased over a factor of time. It was observed that samples containing 1% w/v PAA demonstrated optimal bioadhesivity. Results revealed that incorporation of PAA into alginate-pectinate multi-units successfully improved bioadhesion, without altering buoyancy. Both properties are crucial for the design of the gastroretentive drug delivery system and, therefore, these multi-units may be utilised for the delivery of narrow absorption window drugs (Table 1).

Furthermore, results demonstrated the impact of lyophilization time and polymer concentration on the achievement of gastroretentivity (Table 1). In addition, the above-mentioned formulation variables significantly affected the porosity of the polymeric multi-units. The floating lag time and swelling tendency was determined by the degree of porosity and rate of hydration of the multi-units. Drug release could be maintained over a period of 12 hours with zero order kinetics (n≈0.90) (FIGS. 3 and 4).

All the multi-units were immediately buoyant, remaining buoyant for over 48 hours. Drug entrapment efficacy was desirably high, ranging from 80-95%. The increase in PAA concentrations resulted in an increase in drug release. Results also indicated that the floating lag time and swelling tendency was determined by the degree of porosity and rate of hydration of the multi-units. Drug release was maintained over a period of 12 hours with zero-order kinetics (n≈0.90) (FIG. 3).

The devices remained buoyant in HCl buffer (pH 1.5) and PBS buffer (pH 7.4) for prolonged periods of time (T>48 hours and t≥24 hours respectively). The duration of floatability in the respective buffer media were independent of formulation variables. The devices were able to release drug in two phases with initial up-curving zero-order release phase (65% at $t_{4hours}$) followed by a sustained lag phase (40% at $t_{24hours}$). DEE studies demonstrated entrapment efficiencies between 70-90% (FIGS. 3 and 4).

Twenty seven statistically planned combinations of crosslinked drug-loaded polymeric multi-units were formulated. The polymer concentration ranged from 0.5-2% w/v. The crosslinked, multi-units were subjected to pre-determined lyophilization times. It was observed that the concentration of the polymers employed affected the rigidity of the multi-units. In addition, the lyophilization time impacted on the porosity of the multi-units.

TABLE 1

Floatability of the gastroretentive multi-units

| Formulation Number | Lyophilization Time (Hours) | Duration of Floatation (Hours) |
|---|---|---|
| 1 | 24 | 24 |
| 2 | 13 | 24 |
| 3 | 13 | 24 |
| 4 | 13 | 24 |
| 5 | 24 | 24 |
| 6 | 13 | 24 |
| 7 | 13 | 24 |
| 8 | 24 | 24 |
| 9 | 13 | 24 |
| 10 | 24 | 24 |
| 11 | 2 | 24 |
| 12 | 13 | 24 |
| 13 | 2 | 24 |
| 14 | 2 | 2 |
| 15 | 13 | 24 |
| 16 | 13 | 24 |
| 17 | 13 | 24 |
| 18 | 13 | 24 |
| 19 | 13 | 24 |
| 20 | 2 | 8 |
| 21 | 13 | 24 |
| 22 | 13 | 24 |
| 23 | 24 | 24 |
| 24 | 24 | 24 |
| 25 | 2 | 24 |

TABLE 1-continued

Floatability of the gastroretentive multi-units

| Formulation Number | Lyophilization Time (Hours) | Duration of Floatation (Hours) |
|---|---|---|
| 26 | 13 | 24 |
| 27 | 2 | 24 |

TABLE 2

Textural analysis of the gastroretentive multi-units

| Formulation Number | Lyophilization Time (Hours) | Deformation Energy (J) | Deformability Gradient (N/mm) | Fracture Gradients |
|---|---|---|---|---|
| 1 | 24 | 0.009 | 7.22 | 0.465 |
| 2 | 13 | 0.028 | 13.19 | 1.210 |
| 3 | 13 | 0.021 | 37.89 | 28.510 |
| 4 | 13 | 0.014 | 10.24 | 1.450 |
| 5 | 24 | 0.023 | 5.14 | 0.182 |
| 6 | 13 | 0.098 | 15.47 | 18.970 |
| 7 | 13 | 0.015 | 10.66 | 6.495 |
| 8 | 24 | 0.003 | 6.22 | 0.492 |
| 9 | 13 | 0.033 | 10.22 | 4.960 |
| 10 | 24 | 0.015 | 10.03 | 0.691 |
| 11 | 2 | 0.029 | 18.06 | 12.685 |
| 12 | 13 | 0.006 | 9.19 | 0.922 |
| 13 | 2 | 0.008 | 14.17 | 8.540 |
| 14 | 2 | 0.043 | 1.49 | 0.014 |
| 15 | 13 | 0.066 | 12.56 | 2.250 |
| 16 | 13 | 0.014 | 10.45 | 3.210 |
| 17 | 13 | 0.016 | 8.84 | 0.490 |
| 18 | 13 | 0.009 | 11.33 | 2.900 |
| 19 | 13 | 0.014 | 9.99 | 6.780 |
| 20 | 2 | 0.021 | 23.38 | 10.590 |
| 21 | 13 | 0.033 | 11.46 | 7.840 |
| 22 | 13 | 0.038 | 9.77 | 2.220 |
| 23 | 24 | 0.008 | 9.88 | 1.120 |
| 24 | 24 | 0.022 | 7.04 | 2.180 |
| 25 | 2 | 0 | 0 | 0 |
| 26 | 13 | 0.082 | 19.73 | 2.590 |
| 27 | 2 | 0.015 | 29.92 | 12.590 |

The invention claimed is:

1. An orally administrable gastroretentive pharmaceutical dosage form comprising a plurality of polymeric units, each polymeric unit comprising a cross-linked polymeric matrix which is porous and buoyant in gastric fluid, the polymeric matrix of each polymeric unit comprising:
   alginate,
   pectin,
   polyacrylic acid (PAA), and
   polymeric microparticles comprising polymers which are cross-linked and at least one pharmaceutically active ingredient, wherein at least one of the polymers is a bioadhesive polymeric adjuvant which adheres to the mucosal lining of the stomach and wherein the polymers forming the microparticles comprise chitosan and poly(methacrylate);
   wherein, in use, the plurality of polymeric units initially float on the surface of the gastric fluid, then release the polymeric microparticles; and
   further wherein the microparticles, upon release, adhere to the mucosal surface of the stomach.

2. The dosage form according to claim 1, wherein the polymeric matrix of each polymeric unit further comprises polylactic co-glycolic acid (PLGA).

3. The dosage form according to claim 1, wherein the at least one bioadhesive polymeric adjuvant is selected from hydroxyethylcellulose (HEC), ethylcellulose (EC), hydroxypropylcellulose (HPC) or hydroxypropylmethylcellulose (HPMC), polyethylene oxide (PEO), polyvinyl alcohol (PVA), alginate, chitosan, sodium alginate, pectin, poly(lactic) co-glycolic acid (PLGA), polylactic acid (PLA), poly(methacrylate), polycaprolactone, polyester, polyacrylic acid (PAA), polyamide and glycolide polymers.

4. The dosage form according to claim 2, wherein the at least one bioadhesive polymeric adjuvant is selected from hydroxyethylcellulose (HEC), ethylcellulose (EC), hydroxypropylcellulose (HPC) or hydroxypropylmethylcellulose (HPMC), polyethylene oxide (PEO), polyvinyl alcohol (PVA), alginate, chitosan, sodium alginate, pectin, poly(lactic) co-glycolic acid (PLGA), polylactic acid (PLA), poly(methacrylate), polycaprolactone, polyester, polyacrylic acid (PAA), polyamide and glycolide polymers.

5. The dosage form according to claim 3, wherein the pores in the polymeric matrix are formed by lyophilisation of the polymeric units and/or dosage form.

6. The dosage form according to claim 4, wherein the pores in the polymeric matrix are formed by lyophilisation of the polymeric units and/or dosage form.

7. The dosage form according to claim 1, wherein the pharmaceutically active ingredient has poor bioavailability or a narrow absorption window, and is selected from acyclovir, captopril, riboflavin, levodopa, nitrofurantoin, metformin and ciprofloxacin.

8. The dosage form according to claim 1, wherein the polymeric matrix further comprises a second pharmaceutically active ingredient.

9. The dosage form according to claim 3, wherein the polymeric matrix further comprises a second pharmaceutically active ingredient.

10. The dosage form according to claim 4, wherein the polymeric matrix further comprises a second pharmaceutically active ingredient.

11. The dosage form according to claim 1, wherein the plurality of polymeric units are coated with one or more polymer layers to modulate the release of the pharmaceutically active ingredient.

12. The dosage form according to claim 3, wherein the plurality of polymeric units are coated with one or more polymer layers to modulate the release of the pharmaceutically active ingredient.

13. The dosage form according to claim 4, wherein the plurality of polymeric units are coated with one or more polymer layers to modulate the release of the pharmaceutically active ingredient.

14. The dosage form according to claim 11, which has two layers, the first layer comprising the coated polymeric units and the second layer comprising a rapid release or effervescent layer.

15. The dosage form according to claim 12, which has two layers, the first layer comprising the coated polymeric units and the second layer comprising a rapid release or effervescent layer.

16. The dosage form according to claim 13, which has two layers, the first layer comprising the coated polymeric units and the second layer comprising a rapid release or effervescent layer.

17. The dosage form according to claim 1, which is coated with a polymer which is soluble at a pH of ±1.2 to ensure that effervescence, swelling and adhesion do not occur before the dosage form enters the stomach.

18. The dosage form according to claim 14, which is coated with a polymer which is soluble at a pH of ±1.2 to ensure that effervescence, swelling and adhesion do not occur before the dosage form enters the stomach.

19. The dosage form according to claim 15, which is coated with a polymer which is soluble at a pH of ±1.2 to ensure that effervescence, swelling and adhesion do not occur before the dosage form enters the stomach.

20. The dosage form according to claim 16, which is coated with a polymer which is soluble at a pH of ±1.2 to ensure that effervescence, swelling and adhesion do not occur before the dosage form enters the stomach.

21. A method of manufacturing the gastroretentive pharmaceutical dosage form of claim 1, the method comprising the steps of:
- forming cross-linked polymeric microparticles comprising chitosan and poly(methacrylate) which can adhere to the mucosal lining of the stomach and a pharmaceutically active ingredient;
- forming polymeric units from a cross-linked polymeric matrix comprising at least alginate, pectin, polyacrylic acid and the polymeric microparticles;
- lyophilizing the polymeric units until they are sufficiently porous so as to have a density which enables them to be buoyant in gastric fluid; and
- forming the polymeric units into an orally administrable dosage form.

\* \* \* \* \*